(12) United States Patent
Ebersole et al.

(10) Patent No.: US 11,751,906 B2
(45) Date of Patent: Sep. 12, 2023

(54) ADAPTER FOR USE WITH SURGICAL ACCESS DEVICE FOR EVACUATION OF SMOKE

(71) Applicant: Covidien LP, Mansfield, MA (US)

(72) Inventors: Garrett P. Ebersole, Hamden, CT (US); Jacob C. Baril, Norwalk, CT (US); Justin Thomas, New Haven, CT (US); Matthew A. Dinino, Newington, CT (US); Nicolette R. LaPierre, Windsor Locks, CT (US); Saumya Banerjee, Hamden, CT (US); Roy J. Pilletere, Middletown, CT (US)

(73) Assignee: Covidien LP, Mansfield, MA (US)

( * ) Notice: Subject to any disclaimer, the term of this patent is extended or adjusted under 35 U.S.C. 154(b) by 358 days.

(21) Appl. No.: 17/083,870

(22) Filed: Oct. 29, 2020

(65) Prior Publication Data
US 2022/0133350 A1 May 5, 2022

(51) Int. Cl.
*A61B 17/34* (2006.01)
*A61B 1/313* (2006.01)
*A61B 17/00* (2006.01)

(52) U.S. Cl.
CPC ........ *A61B 17/3423* (2013.01); *A61B 1/3132* (2013.01); *A61B 2017/00486* (2013.01); *A61B 2017/3425* (2013.01); *A61B 2218/008* (2013.01)

(58) Field of Classification Search
CPC .......... A61B 17/3423; A61B 2218/008; A61B 2017/00486
USPC .................................................. 600/184–245
See application file for complete search history.

(56) References Cited

U.S. PATENT DOCUMENTS

| 397,060 | A | 1/1889 | Knapp |
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |

(Continued)

FOREIGN PATENT DOCUMENTS

| EP | 0480653 A1 | 4/1992 |
| EP | 0610099 A2 | 8/1994 |

(Continued)

OTHER PUBLICATIONS

International Search Report dated Dec. 1, 2021 issued in corresponding PCT Appln. No. PCT/US2021/054654.

*Primary Examiner* — Eduardo C Robert
*Assistant Examiner* — Tara Rose E Carter
(74) *Attorney, Agent, or Firm* — Carter, DeLuca & Farrell LLP

(57) ABSTRACT

An evacuation adapter for use with a surgical access device includes a distal section selectively engageable with a proximal section. The distal section and the proximal section each include a base, an outer ring, and an inner ring. Each base defines a central opening. Each outer ring defines at least one opening. Each inner ring defines at least one opening. The outer ring of the proximal section includes a port. The proximal section is rotatable relative to the distal section between a first position where fluid is able to flow from the central opening of the distal section through the port, and a second position where fluid is blocked from flowing from the central opening of the distal section through the port.

21 Claims, 6 Drawing Sheets

(56) References Cited

U.S. PATENT DOCUMENTS

| | | |
|---|---|---|
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Mair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 8,454,645 B2 | 6/2013 | Criscuolo et al. |

(56) References Cited

U.S. PATENT DOCUMENTS

| | | | | |
|---|---|---|---|---|
| 2015/0031958 A1* | 1/2015 | Kleyman | ........... | A61B 17/3423 |
| | | | | 600/204 |
| 2015/0173792 A1* | 6/2015 | McGinley | .......... | A61B 17/3423 |
| | | | | 600/204 |
| 2020/0113552 A1* | 4/2020 | Rioux | ................ | A61B 17/3423 |
| 2021/0267639 A1* | 9/2021 | Fischer | ............... | A61M 13/003 |

FOREIGN PATENT DOCUMENTS

| | | |
|---|---|---|
| EP | 0880939 A1 | 12/1998 |
| EP | 1188415 A2 | 3/2002 |
| EP | 3360494 A1 | 8/2018 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2020036497 A1 | 2/2020 |

\* cited by examiner

ADAPTER FOR USE WITH SURGICAL ACCESS DEVICE FOR EVACUATION OF SMOKE

BACKGROUND

Technical Field

The present disclosure relates to an adapter for use with a surgical access device. More particularly, the present disclosure relates to an adapter for use with a surgical access device to facilitate the evacuation of smoke from a surgical site.

Background of Related Art

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e., a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall and is then removed to permit introduction of additional surgical instrumentation through the surgical access device to perform the surgical procedure.

During these procedures, it may be challenging to minimize smoke (including gas and other particulates) that escapes from the pressurized body cavity when one instrument is removed from the surgical access device and prior to the introduction of another surgical device through the surgical access device, for instance. Smoke may be created during electrosurgical procedures, and/or particulates may be present while removing surgical instruments from an access device, for example.

Accordingly, it may be helpful to provide an adapter that engages a surgical access device, and that can help control evacuation of smoke from the surgical site.

SUMMARY

The present disclosure relates to an evacuation adapter for use with a surgical access device. The evacuation adapter includes a distal section and a proximal section. The distal section is configured to selectively engage a proximal end of a surgical access device, and includes a base, an outer ring, and an inner ring. The base defines a central opening. The outer ring extends proximally from the base and defines at least one opening. The inner ring extends proximally from the base and defines at least one opening. The proximal section is configured to selectively engage the distal section, and includes a base, an outer ring, and an inner ring. The base defines a central opening. The outer ring extends distally from the base and includes a port. The inner ring extends distally from the base and defines at least one opening. When the proximal section is engaged with the distal section, the proximal section is rotatable relative to the distal section between a first position where fluid is able to flow from the central opening of the distal section through the port of the proximal section, and a second position where fluid is blocked from flowing from the central opening of the distal section through the port of the proximal section.

In aspects, when the proximal section is in the first position, at least a portion of the at least one opening of the inner ring of the proximal section may be radially aligned with at least a portion of the at least one opening of the inner ring of the distal section. Further, in aspects, when the proximal section is in the first position, at least a portion of the opening of the outer ring of the distal section may be radially aligned with at least a portion of the port of the proximal section.

Additionally, in aspects, when the proximal section is in the second position, at least one opening of the inner ring of the proximal section may be radially offset from the at least one opening of the inner ring of the distal section. Further, in aspects, when the proximal section is in the second position, the opening of the outer ring of the distal section may be radially offset from the port of the proximal section.

In additional aspects, a distal portion of the inner ring of the proximal section may include at least one finger extending radially outward therefrom, and the distal section may include a circular slot. The at least one finger of the inner ring of the proximal section may be configured to slide within the circular slot of the distal section.

In disclosed aspects, the at least one opening of the inner ring of the distal section may include four openings, and the at least one opening of the inner ring of the proximal section may include four openings.

In aspects, the proximal section may include at least one stop member extending distally from the base of the proximal section, and the distal section may include at least one wall extending radially inward from the outer ring. A predetermined amount of rotation of the proximal section relative to the distal section may cause the at least one stop member to contact the at least one wall. Further, in aspects, the at least one stop member may be in contact with the at least one wall when the proximal section is in the second position.

Additionally, in aspects, the evacuation adapter may include a poka-yoke assembly configured to ensure the proximal section engages the distal section in a proper radial orientation.

The present disclosure also relates to a surgical system including a surgical access device and an evacuation adapter. The surgical access device includes a cannula having a housing, an elongated portion extending distally from the housing and defining a longitudinal axis, and a central channel configured to allow at least a portion of a surgical instrument to pass therethrough. The evacuation adapter is configured to selectively engage the housing of the surgical access device, and includes a distal section, a proximal section, and a port. The distal section includes a base, an outer ring extending proximally from the base, and an inner ring extending proximally from the base. The base defines a central opening. The inner ring defines at least one window, and the outer ring defines at least one window. The proximal section is configured to selectively engage the distal section and includes a base, an outer ring extending distally from the base, and an inner ring extending distally from the base. The base defines a central opening. The inner ring defines at least one window. The port is configured to engage a suction device. When the proximal section is engaged with the distal section and when the evacuation adapter is engaged with the housing of the cannula, the proximal section is rotatable relative to the distal section between a first position where fluid is able to flow from the central channel of the cannula through the port of the evacuation adapter, and a second position where fluid is blocked from flowing from the central channel of the cannula through the port of the evacuation adapter.

In aspects, when the proximal section of the evacuation adapter is in the first position, at least a portion of the at least one window of the inner ring of the proximal section may be radially aligned with at least a portion of the at least one window of the inner ring of the distal section, and at least a portion of the window of the outer ring of the distal section may be radially aligned with at least a portion of the port. Further, in aspects, when the proximal section of the evacuation adapter is in the second position, at least one window of the inner ring of the proximal section may be radially offset from the at least one window of the inner ring of the distal section, and the window of the outer ring of the distal section may be radially offset from the port.

In disclosed aspects, a distal portion of the inner ring of the proximal section of the evacuation adapter may include at least one finger extending radially outward therefrom, the distal section of the evacuation adapter may include a circular slot, and the at least one finger of the inner ring of the proximal section may be configured to slide within the circular slot of the distal section.

Further, in aspects, the proximal section of the evacuation adapter may include at least one stop member extending distally from the base of the proximal section. The distal section of the evacuation adapter may include at least one wall extending radially inward from the outer ring. A predetermined amount of rotation of the proximal section relative to the distal section may cause the at least one stop member to contact the at least one wall. Additionally, in aspects, the at least one stop member may be in contact with the at least one wall when the proximal section of the evacuation adapter is in the second position.

In aspects, the evacuation adapter may include a poka-yoke assembly configured to ensure the proximal section engages the distal section in a proper radial orientation.

DESCRIPTION OF THE DRAWINGS

Various aspects of the present disclosure are illustrated herein with reference to the accompanying drawings, wherein.

DETAILED DESCRIPTION

Figure 1:
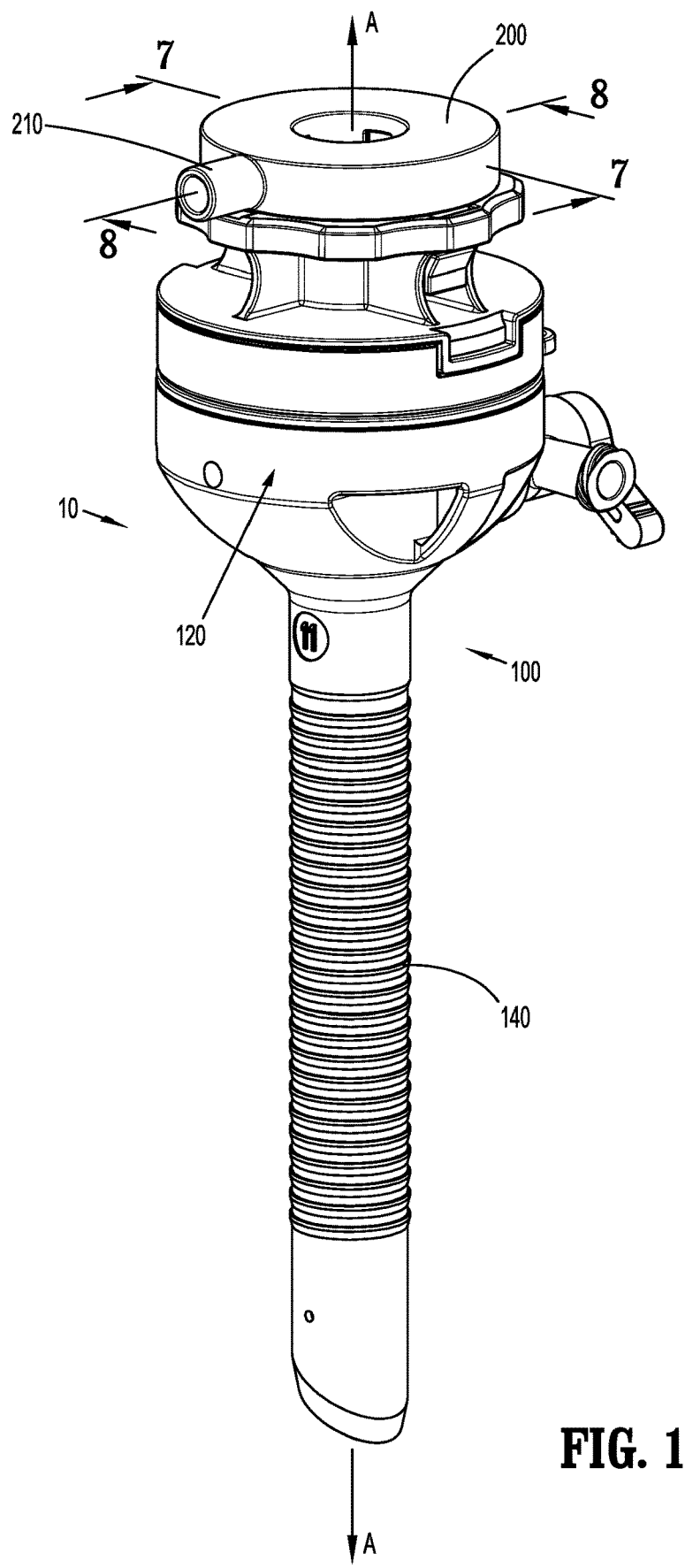
FIG. 1 is a perspective view of an evacuation adapter of the present disclosure engaged with a surgical access device.

Aspects of the presently disclosed evacuation adapter for use with a surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Generally, a surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a housing of the cannula. In this initial configuration, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The housing of the cannula may include seals or valves that help prevent the escape of insufflation gases from the body cavity, while also allowing surgical instruments to be inserted into the body cavity.

However, during the removal of surgical instruments from the surgical access device, for instance, smoke, air fluid, gas, particulates, etc. (hereinafter collectively referred to as "smoke") may still escape from the body cavity (or from the surgical instrument itself) through the seal(s) or valve(s) of the surgical access device. Additionally, the use of electrosurgical instruments may create smoke within the body cavity. The evacuation adapter of the present disclosure helps minimize the amount of smoke being expelled from surgical access device and into the surrounding environment.

FIGS. 1-10 illustrate an evacuation adapter according to the present disclosure. With initial reference to FIG. 1, the evacuation adapter 200 is shown engaged with a proximal end of a surgical access device 10. Generally, the surgical access device 10 includes a cannula body 100 having a housing 120 at its proximal end and an elongated portion 140 extending distally from the housing 120. The elongated portion 140 defines a channel 150 (FIGS. 7 and 8) extending therethrough, and defines a longitudinal axis "A-A." A seal assembly 160 including a first seal 162 and a second seal 164 (FIGS. 7 and 8) is housed at least partially within the housing 120. An obturator (not shown) is insertable through the channel 150 and is engageable with the housing 120 (when the evacuation adapter 200 is not engaged with the surgical access device 10), for instance. Additionally, while the evacuation adapter 200 is shown in connection with the particular type surgical access device 10, the evacuation adapter 200 of the present disclosure can also be used with other types of surgical access devices.

Figure 2:
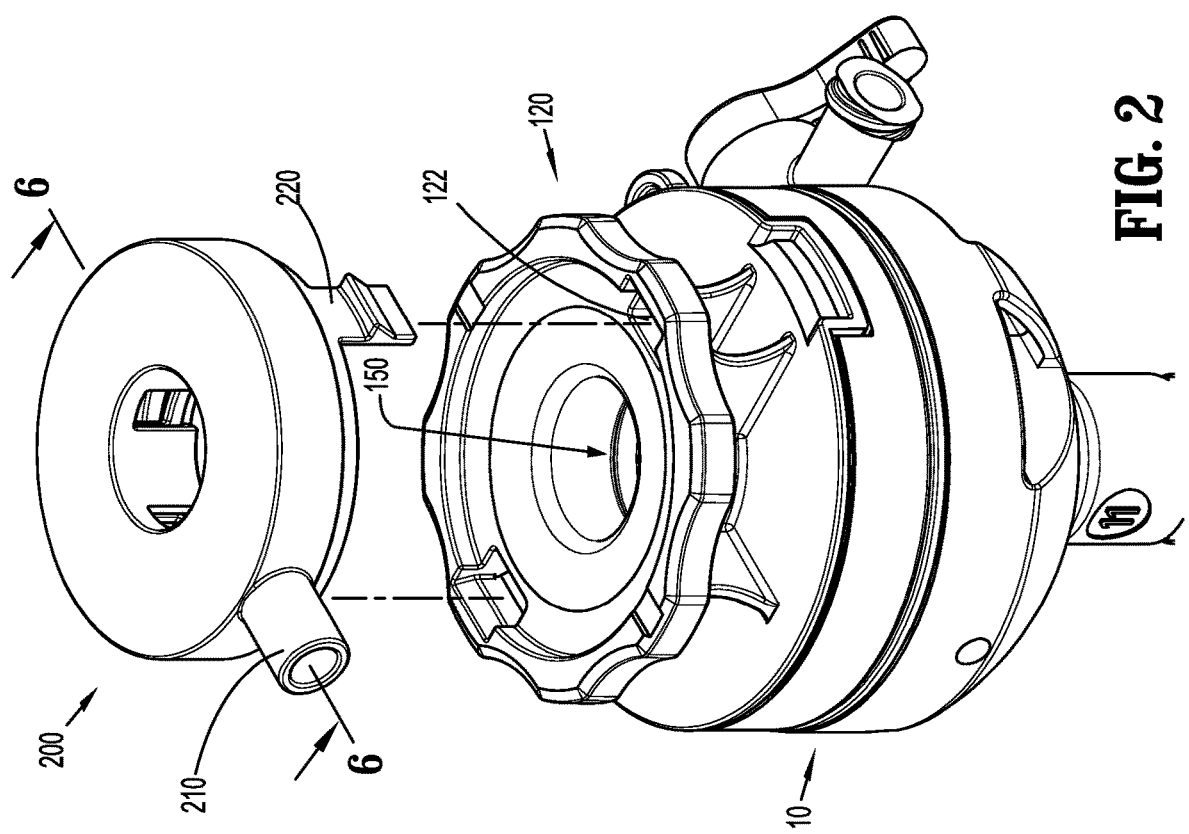
FIG. 2 is an assembly view of the evacuation adapter and a proximal portion of the surgical access device of FIG. 1.

With particular reference to FIG. 2, the evacuation adapter 200 is selectively engageable with the housing 120 of the surgical access device 10. The evacuation adapter 200 includes a port 210 configured to engage a hose of a vacuum source (not explicitly shown). When engaged with the surgical access device 10 and with a vacuum source, the evacuation adapter 200 is able to remove smoke from within the channel 150 of the surgical access device 10 and/or remove particulates from a surgical instrument being removed therefrom.

Figure 3:
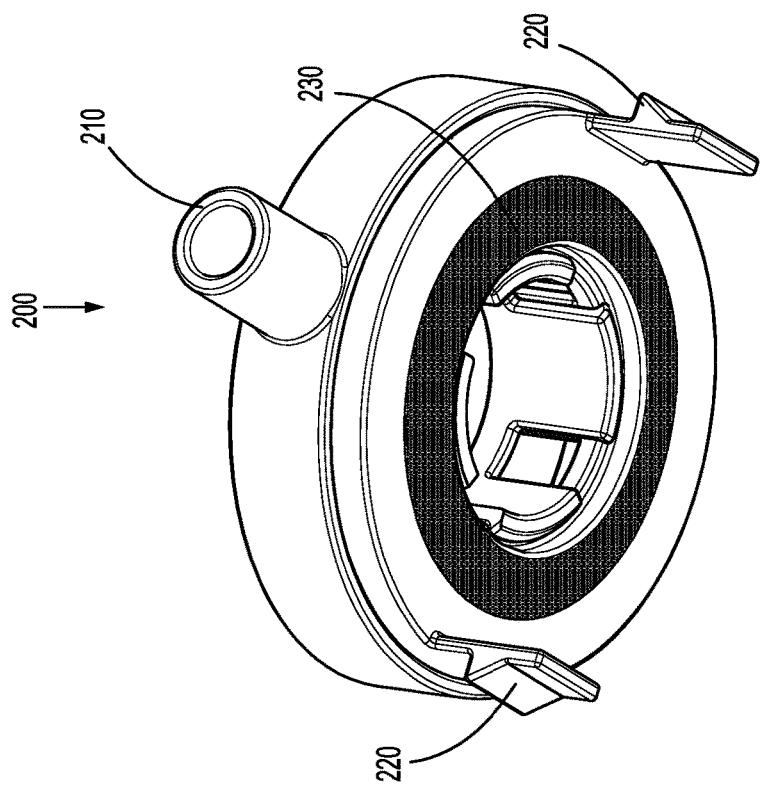
FIG. 3 is a perspective view of the evacuation adapter of FIG. 1.

As shown in FIGS. 2 and 3, the evacuation adapter 200 includes a pair of legs 220 configured to selectively lockingly engage a corresponding pair of apertures 122 within the housing 120 of the cannula body 100, e.g., in a snap-fit engagement. The evacuation adapter 200 also includes a gasket 230 on a distal section thereof (e.g., at least partially within a recess). When the evacuation adapter 200 is engaged with the housing 120, the gasket 230 is configured to provide a seal to help prevent smoke from escaping between the evacuation adapter 200 and the housing 120.

Figure 4:
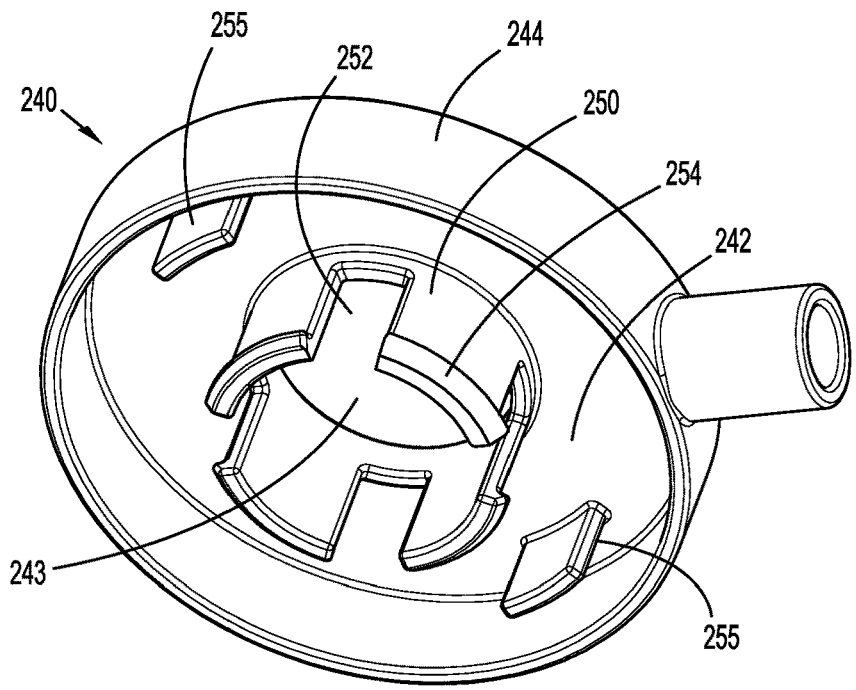
FIG. 4 is a perspective view of a proximal section of the evacuation adapter of FIG. 1.
Figure 5:
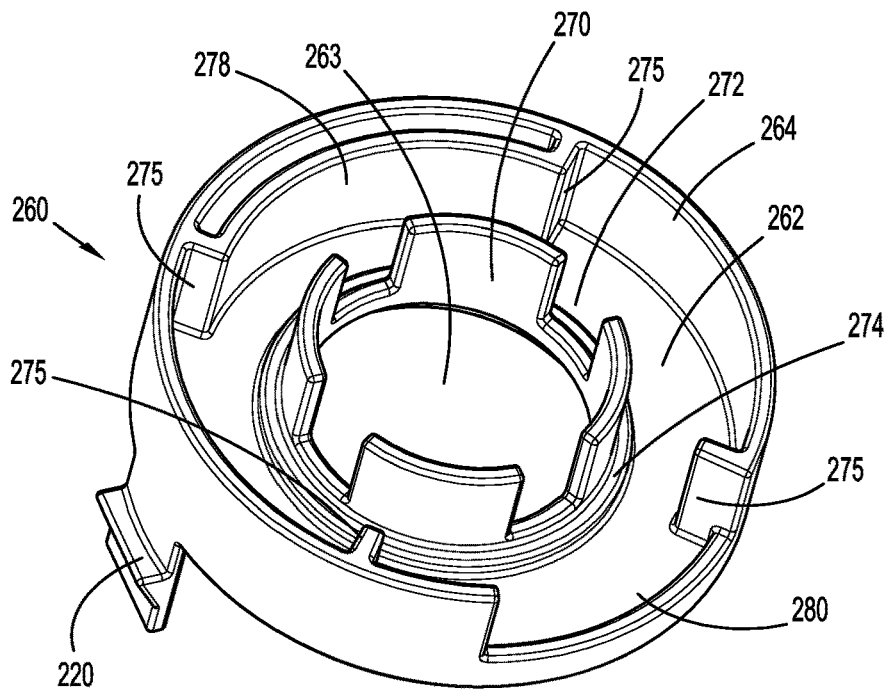
FIG. 5 is a perspective view of a distal section of the evacuation adapter of FIG. 1.

Referring now to FIGS. 4 and 5, two portions of the evacuation adapter 200 are shown. More particularly, FIG. 4 illustrates a proximal section 240 of the evacuation adapter 200, and FIG. 5 illustrates a distal section 260 of the evacuation adapter 200. The proximal section 240 of the evacuation adapter 200 is configured to rotatably engage the distal section 260 of the evacuation adapter 200.

More particularly, when the proximal section 240 is mechanically engaged with the distal section 260, and when the evacuation adapter 200 is mechanically engaged with the housing 120 of the cannula body 100, the proximal section 240 of the evacuation adapter 200 is configured to rotate about the longitudinal axis "A-A" relative to the distal section 260 of the evacuation adapter 200 and relative to the housing 120 of the cannula body 100 of the surgical access device 10.

As will be described in further detail below, the engagement between fingers 254 of the proximal section 240 of the evacuation adapter 200, and a circular groove or slot 274 of the distal section 260 of the evacuation adapter 200 enable the rotation between the proximal section 240 and the distal section 260. As will also be described in further detail below, the rotation of the proximal section 240 relative to the distal section 260 allows a user to control the flow of smoke from the channel 150 of the cannula body 100 through the port 210 of the evacuation adapter 200.

With particular reference to FIG. 4, the proximal section 240 of the evacuation adapter 200 is shown. The proximal section 240 includes a base 242 defining a central opening 243, an outer ring 244 extending distally from an outer circumference of the base 242, an inner ring 250 extending distally from an inner circumference of the base 242 and adjacent the central opening 243, stop members 255 extending distally from the base 242, and the port 210 extending laterally outward from the outer ring 244.

With continued reference to FIG. 4, the inner ring 250 includes a plurality of windows or openings 252 defined therein. While the four openings 252 are shown in the exemplary structure illustrated, more or fewer openings 252 may be included without departing from the scope of the present disclosure. Additionally, a distal end of the inner ring 250 includes the fingers 254 extending radially outward therefrom.

Referring now to FIG. 5, the distal section 260 of the evacuation adapter 200 is shown. The distal section 260 includes a base 262 defining a central opening 263, an outer ring 264 extending proximally from an outer circumference of the base 262, an inner ring 270 extending proximally from an inner circumference of the base 262 and adjacent the central opening 263, radial walls 275 extending proximally from the base 262 and radially inward from the outer ring 264, a poka-yoke assembly 278 extending radially inward from the outer ring 264 between two adjacent radial walls 275, a window or opening 280 defined in the outer ring 264, and the legs 220 extending distally from the outer ring 264.

With continued reference to FIG. 5, the inner ring 270 of the distal section 260 includes a plurality of windows or openings 272 defined therein. While the four openings 272 are shown in the exemplary structure illustrated, more or fewer openings 272 may be included without departing from the scope of the present disclosure. Additionally, the circular groove or slot 274 is defined adjacent the central opening 263 of the distal section 260 and distally of the inner ring 270 (see also FIG. 6).

Figure 6:
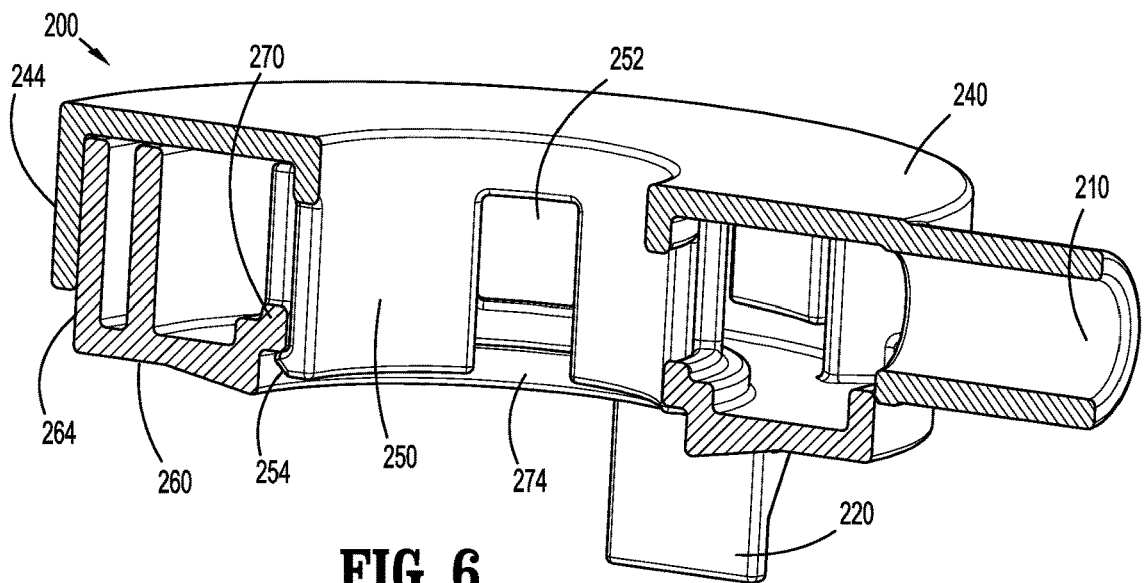
FIG. 6 is a cross-sectional view of the evacuation adapter taken along section line 6-6 in FIG. 2.
Figure 7:
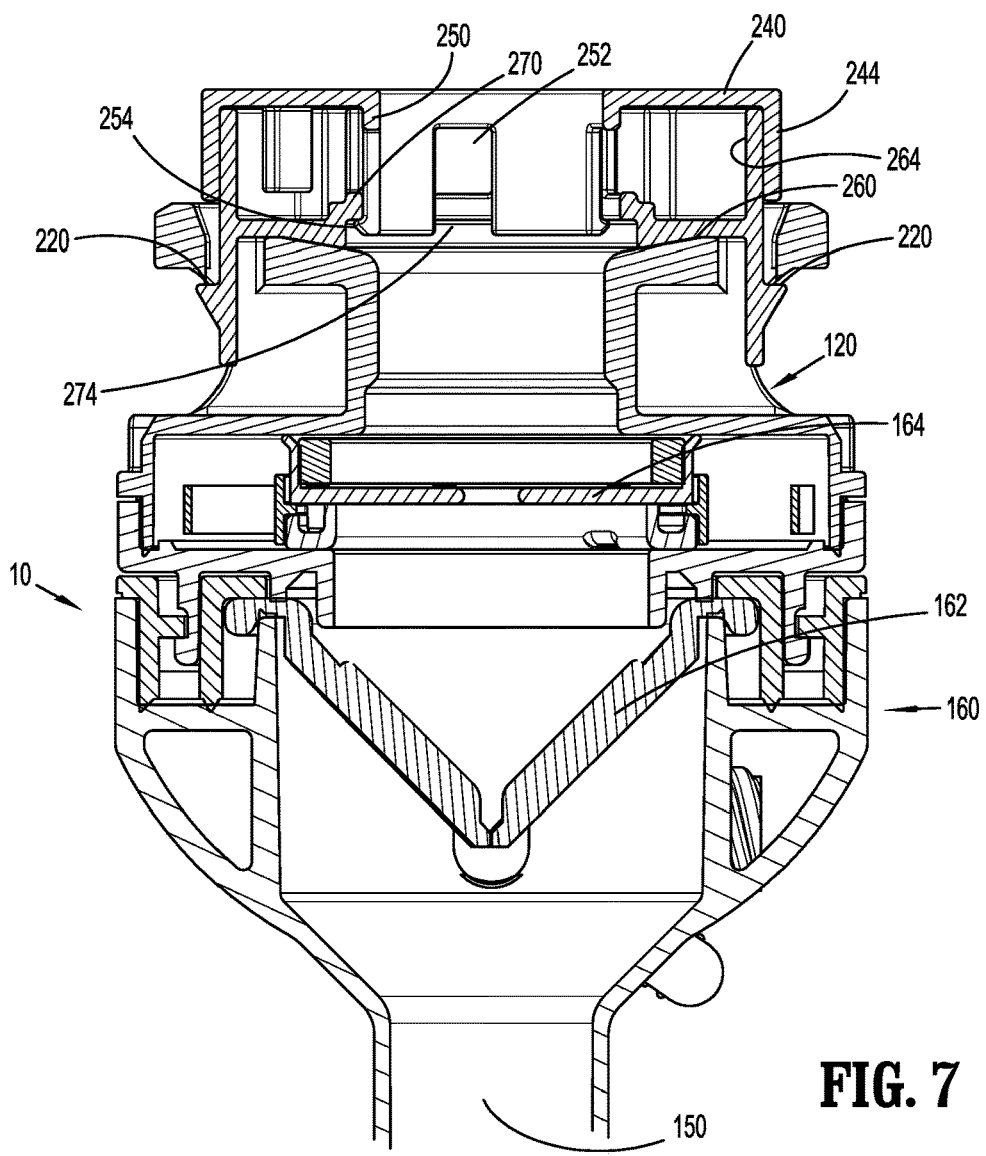
FIGS. 7 and 8 are cross-sectional views of the evacuation adapter taken along section lines 7-7 and 8-8, respectively, in FIG. 1 engaged with the surgical access device.
Figure 8:
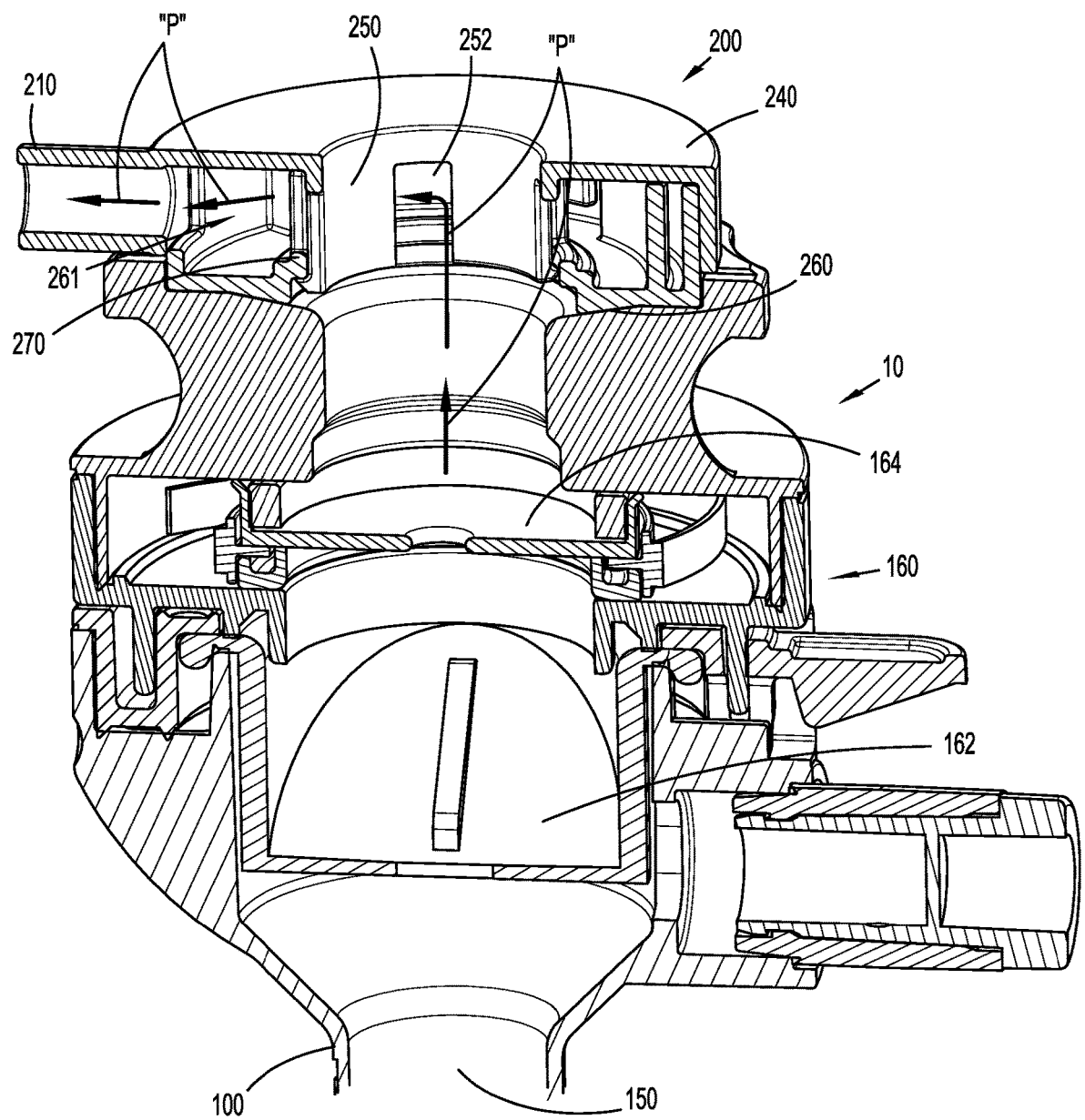

With reference to FIGS. 6-8, the engagement between the proximal section 240 and the distal section 260 of the evacuation adapter 200 is shown. Generally, the proximal section 240 and the distal section 260 are approximated or moved toward each other such that the outer ring 244 of the proximal section 240 is positioned radially outward of the outer ring 264 of the distal section 260, and the inner ring 250 of the proximal section 240 is positioned radially inward of the inner ring 270 of the distal section 260. Additionally, after a predetermined amount of approximation between the proximal section 240 and the distal section 260, the fingers 254 of the inner ring 250 of the proximal section 240 engage the circular slot 274 of the distal section 260. This engagement between the fingers 254 and the circular slot 274 selectively locks the longitudinal position of the proximal section 240 relative to the distal section 260. Additionally, the fingers 254 are configured to slide within the circular slot 274 when the proximal section 240 rotates about the longitudinal axis "A-A" relative to the distal section 260.

Figure 9:
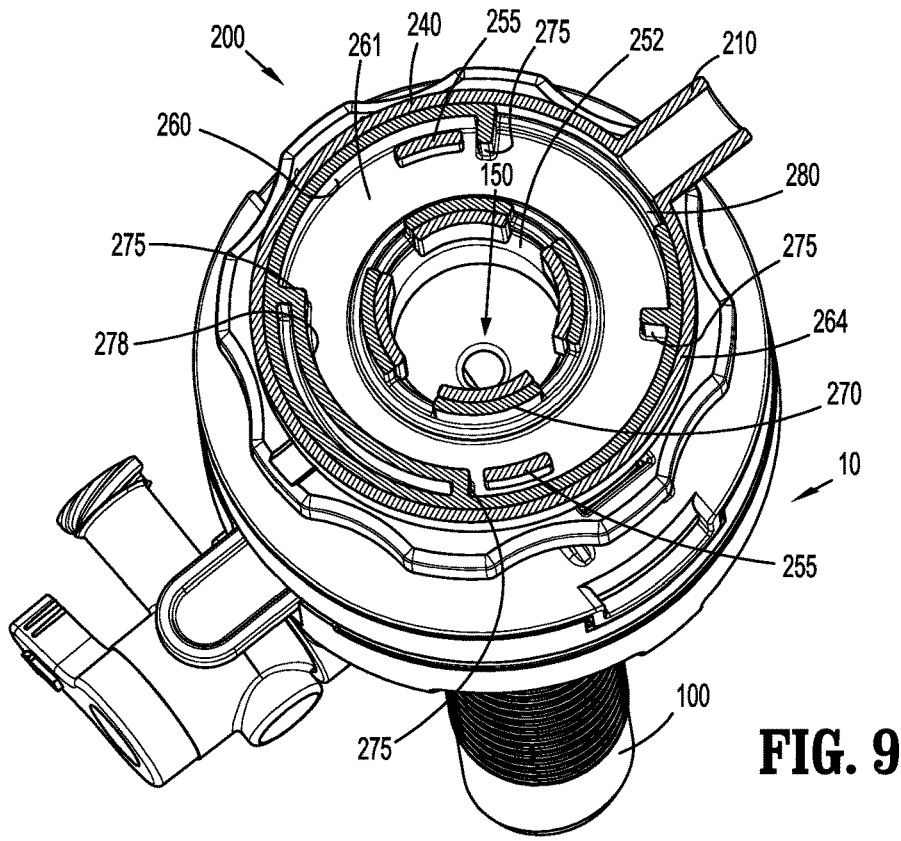
FIG. 9 is a top, perspective view of the evacuation adapter of FIG. 1 in an open position and engaged with the surgical access device of FIG. 1.
Figure 10:
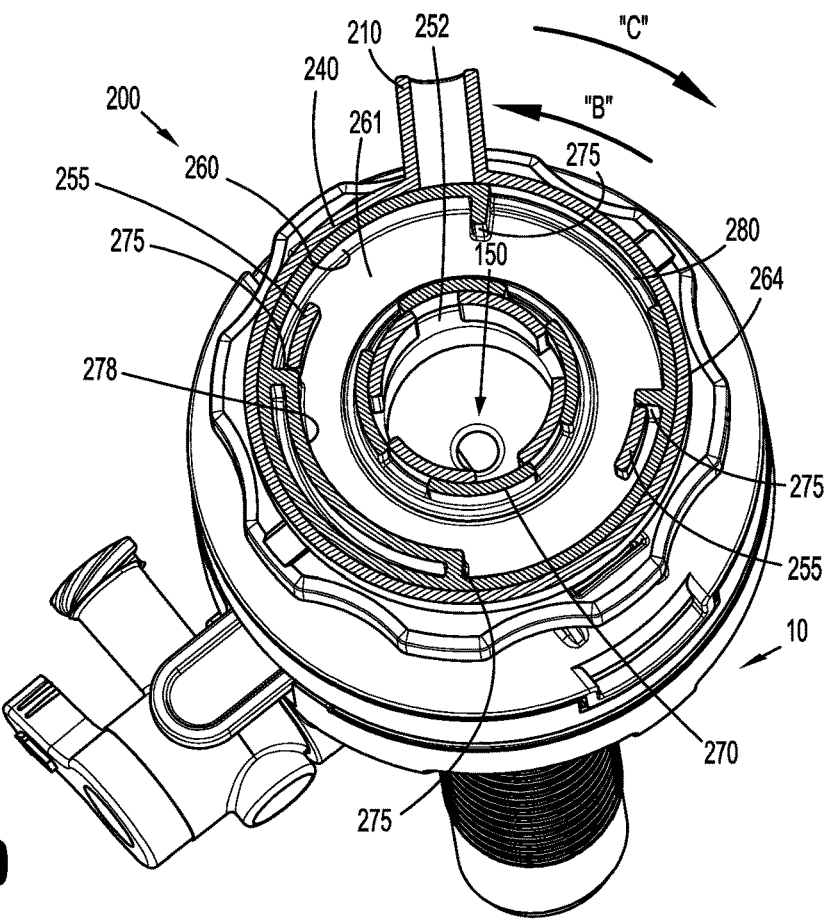
FIG. 10 is a top, perspective view of the evacuation adapter of FIG. 1 in a closed position and engaged with the surgical access device of FIG. 1.

Referring now to FIGS. 8-10, a fluid flow path "P" through the evacuation adapter 200 is shown. The rotation of the proximal section 240 relative to the distal section 260 allows a user to control the flow of fluid (including gas, air, particulates, and smoke, for instance) from the channel 150 of the cannula body 100 through the port 210 of the evacuation adapter 200. That is, the evacuation adapter 200 is movable between an open position (FIGS. 8 and 9), where fluid is able to flow from the channel 150 of the cannula body 100 and into the port 210, and a closed position (FIG. 10), where the evacuation adapter 200 blocks the fluid from flowing from the channel 150 of the cannula body 100 through the port 210.

More particularly, when the openings 252 of the inner ring 250 of the proximal section 240 are radially aligned with the openings 272 of the inner ring 270 of the distal section 260 (FIGS. 8 and 9), the opening 280 of the outer ring 264 of the distal section 260 is radially aligned with the port 210, and smoke is able to flow from the channel 150, through the openings 252 and 272, through a cavity 261 defined between the outer ring 264 and the inner ring 270 of the distal section 260, through the opening 280 of the outer ring 264 of the distal section 260, and through the port 210 of the evacuation adapter 200.

FIG. 10 depicts the rotation of the proximal section 240 relative to the distal section 260 of the evacuation adapter 200 in the general direction of arrow "B" from its position shown in FIG. 9. In this position, the openings 252 of the inner ring 250 of the proximal section 240 are radially offset with the openings 272 of the inner ring 270 of the distal section 260. Thus, smoke is prevented from entering the cavity 261 of the distal section 260. Additionally, in this position, the opening 280 of the outer ring 264 of the distal section 260 is radially offset from the port 210 such that the port 210 is occluded, thereby preventing smoke from travelling from the cavity 261 through the port 210. Accordingly, rotation of the proximal section 240 relative to the distal section 260 allows a user to control the flow of smoke from the channel 150 of the cannula body 100 through the port 210 of the evacuation adapter 200.

Referring now to FIGS. 9 and 10, the stop members 255 of the proximal section 240 and the radial walls 275 of the distal section 260 of the evacuation adapter 200 are shown. The stop members 255 and the radial walls 275 help limit the amount of rotation of the proximal section 240 relative to the distal section 260. For example, FIG. 10 illustrates when the proximal section 240 has been fully rotated relative to the distal section 260 in the general direction of arrow "B." Here, the stop members 255 of the proximal section 240 are in contact with the radial walls 275 of the distal section 260, thereby preventing additional rotation of the proximal section 240 relative to the distal section 260 in the general direction of arrow "B." Additionally, when the proximal section 240 is rotated a predetermined amount relative to the distal section 260 in the opposite direction, i.e., in the general direction of arrow "C" in FIG. 10, the stop members 255 of the proximal section 240 make contact with the (other) radial walls 275 of the distal section 260, thereby preventing additional rotation therebetween.

With continued reference to FIGS. 9 and 10, the poka-yoke assembly 278 is shown. Poka-yoke assembly 278 helps ensure the proximal section 240 and the distal section 260 of the evacuation assembly 200 are assembled in the proper radial orientation. That is, for example, the poka-yoke assembly 278 ensures that the port 210 of the proximal section 240 is generally on the same radial side of the channel 150 of the cannula body 100 as the opening 280 of the outer ring 264. The orientation and positioning of the poka-yoke assembly 278 and the stop members 255 prevents incorrect assembly of proximal section 240 and the distal section 260 of the evacuation assembly 200, as the proximal section 240 is only physically engageable with the distal section 260 in the proper radial orientation. More particularly, if a user attempted to engage the proximal section 240 with the distal section 260 in the incorrect orientation (e.g., rotated approximately 180° from the illustrated orientation), the contact between the stop members 255 and the poka-yoke assembly 278 would physically prevent such an incorrect assembly attempt.

In use, a user approximates the proximal section 240 of the evacuation adapter 200 with the distal section 260 until the fingers 254 of the proximal section 240 engage the circular slot 274 of the distal section 260. The evacuation adapter 200 is connected to the surgical access device 10 by engaging the legs 220 of the evacuation adapter 200 with the apertures 122 of the housing 120 of the cannula body 100. A suction device is engaged with the port 210 of the evacuation adapter 200.

A user may insert an obturator through the central openings 243, 263 of the proximal section 240 and the distal section 260, respectively, of the evacuation adapter 200, through the channel 150 of the cannula body 100, and into tissue. Next, prior to removal of the obturator from the surgical access device 10, the user can ensure the evacuation adapter 200 is in its first, open position by rotating the proximal section 240 of the evacuation adapter 200 relative to the distal section 260, if necessary. In this position, the obturator is removed from the surgical access device 10 and the suction device is able to remove any smoke that may exit the surgical access device 10 (e.g., through seals 162, 164 (FIGS. 7 and 8) within the housing 120), prior to the smoke becoming airborne (e.g., within the operating room).

A user may then insert another surgical instrument through the central openings 243, 263 of the proximal section 240 and the distal section 260, respectively, of the evacuation adapter 200, through the channel 150 of the cannula body 100, and into tissue. When the surgical instrument is within tissue, the user may rotate the proximal section 240 of the evacuation adapter 200 relative to the distal section 260 to move the evacuation adapter 200 to its second, closed position such that the suction device does not impact the pressurized body cavity, for instance.

As can be appreciated, the user can move the evacuation adapter 200 to the open or closed position (or a partially-open position) as many times as desired during a surgical operation to help control the amount of smoke that becomes airborne.

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. An evacuation adapter for use with a surgical access device, the evacuation adapter comprising:
   a distal section configured to engage a proximal end of a surgical access device, the distal section including a base, an outer ring extending proximally from the base, and an inner ring extending proximally from the base, the base defining a central opening, the inner ring defining at least one opening, and the outer ring defining at least one opening; and
   a proximal section configured to selectively engage the distal section and including a base, an outer ring extending distally from the base, at least one stop member extending distally from the base, and an inner ring extending distally from the base, the base defining a central opening, the inner ring defining at least one opening, and the outer ring including a port,
   wherein when the proximal section is engaged with the distal section, the proximal section is rotatable relative to the distal section between a first position where fluid is able to flow from the central opening of the distal section through the port of the proximal section, and a second position where fluid is blocked from flowing from the central opening of the distal section through the port of the proximal section.

2. The evacuation adapter according to claim 1, wherein when the proximal section is in the first position, at least a portion of the at least one opening of the inner ring of the proximal section is radially aligned with at least a portion of the at least one opening of the inner ring of the distal section.

3. The evacuation adapter according to claim 2, wherein when the proximal section is in the first position, at least a portion of the opening of the outer ring of the distal section is radially aligned with at least a portion of the port of the proximal section.

4. The evacuation adapter according to claim 2, wherein when the proximal section is in the second position, at least one opening of the inner ring of the proximal section is radially offset from the at least one opening of the inner ring of the distal section.

5. The evacuation adapter according to claim 4, wherein when the proximal section is in the second position, the opening of the outer ring of the distal section is radially offset from the port of the proximal section.

6. The evacuation adapter according to claim 1, wherein a distal portion of the inner ring of the proximal section includes at least one finger extending radially outward from the inner ring of the proximal section.

7. The evacuation adapter according to claim 6, wherein the distal section includes a circular slot, and the at least one finger of the inner ring of the proximal section is configured to slide within the circular slot of the distal section.

8. The evacuation adapter according to claim 1, wherein the at least one opening of the inner ring of the distal section includes four openings.

9. The evacuation adapter according to claim 8, wherein the at least one opening of the inner ring of the proximal section includes four openings.

10. The evacuation adapter according to claim 1, wherein the distal section includes at least one wall extending radially inward from the outer ring, a predetermined amount of rotation of the proximal section relative to the distal section causes the at least one stop member to contact the at least one wall.

11. The evacuation adapter according to claim 10, wherein the at least one stop member is in contact with the at least one wall when the proximal section is in the second position.

12. The evacuation adapter according to claim 1, further including a poka-yoke assembly configured to ensure the proximal section engages the distal section in a proper radial orientation.

13. A surgical system, comprising:
a surgical access device having a cannula including a housing, an elongated portion extending distally from the housing and defining a longitudinal axis, and a central channel configured to allow at least a portion of a surgical instrument to pass through the central channel; and
an evacuation adapter configured to selectively engage the housing of the surgical access device, the evacuation adapter including:
a distal section having a base, an outer ring extending proximally from the base, and an inner ring extending proximally from the base, the base defining a central opening, the inner ring defining at least one window, and the outer ring defining at least one window;
a proximal section configured to selectively engage the distal section and including a base, an outer ring extending distally from the base, and an inner ring extending distally from the base, the base defining a central opening, the inner ring defining at least one window; and
a port configured to engage a suction device,
wherein when the proximal section is engaged with the distal section and when the evacuation adapter is engaged with the housing of the cannula, the proximal section is rotatable relative to the distal section between a first position where fluid is able to flow from the central channel of the cannula through the port of the evacuation adapter, and a second position where fluid is blocked from flowing from the central channel of the cannula through the port of the evacuation adapter.

14. The surgical device according to claim 13, wherein when the proximal section of the evacuation adapter is in the first position, at least a portion of the at least one window of the inner ring of the proximal section is radially aligned with at least a portion of the at least one window of the inner ring of the distal section, and at least a portion of the window of the outer ring of the distal section is radially aligned with at least a portion of the port.

15. The surgical device according to claim 14, wherein when the proximal section of the evacuation adapter is in the second position, at least one window of the inner ring of the proximal section is radially offset from the at least one window of the inner ring of the distal section, and the window of the outer ring of the distal section is radially offset from the port.

16. The surgical device according to claim 13, wherein a distal portion of the inner ring of the proximal section of the evacuation adapter includes at least one finger extending radially outward therefrom from the inner ring of the proximal section, and the distal section of the evacuation adapter includes a circular slot, and wherein the at least one finger of the inner ring of the proximal section is configured to slide within the circular slot of the distal section.

17. The surgical device according to claim 13, wherein the proximal section of the evacuation adapter includes at least one stop member extending distally from the base of the proximal section and the distal section of the evacuation adapter includes at least one wall extending radially inward from the outer ring, and wherein a predetermined amount of rotation of the proximal section relative to the distal section causes the at least one stop member to contact the at least one wall.

18. The surgical device according to claim 17, wherein the at least one stop member is in contact with the at least one wall when the proximal section of the evacuation adapter is in the second position.

19. The surgical device according to claim 13, wherein the evacuation adapter includes a poka-yoke assembly configured to ensure the proximal section engages the distal section in a proper radial orientation.

20. An evacuation adapter for use with a surgical access device, the evacuation adapter comprising:
a distal section configured to engage a proximal end of a surgical access device, the distal section including a base, an outer ring extending proximally from the base, and an inner ring extending proximally from the base, the base defining a central opening, the inner ring defining at least one opening, and the outer ring defining at least one opening;
a proximal section configured to selectively engage the distal section and including a base, an outer ring extending distally from the base, and an inner ring extending distally from the base, the base defining a central opening, the inner ring defining at least one opening, and the outer ring including a port; and
a poka-yoke assembly configured to ensure the proximal section engages the distal section in a proper radial orientation,
wherein when the proximal section is engaged with the distal section, the proximal section is rotatable relative to the distal section between a first position where fluid is able to flow from the central opening of the distal section through the port of the proximal section, and a second position where fluid is blocked from flowing from the central opening of the distal section through the port of the proximal section.

21. An evacuation adapter for use with a surgical access device, the evacuation adapter comprising:
a distal section configured to engage a proximal end of a surgical access device, the distal section including a base, an outer ring extending proximally from the base, and an inner ring extending proximally from the base, the base defining a central opening, the inner ring defining at least one opening, and the outer ring defining at least one opening; and a proximal section configured to selectively engage the distal section and including a base, an outer ring extending distally from the base, and an inner ring extending distally from the base, the base defining a central opening, the inner ring defining at least one opening, and the outer ring including a port, wherein when the proximal section is engaged with the distal section, the proximal section is rotatable relative to the distal section between a first position where fluid is able to flow from the central opening of the distal section through the port of the proximal section, and a second position where fluid is blocked from flowing from the central opening of the distal section through the port of the proximal section, when the proximal section is in the first position, at least a portion of the at least one opening of the inner ring of the proximal section is radially aligned with at least a portion of the at least one opening of the inner ring of the distal section, and when the proximal section is in the second position, at least one opening of the inner ring of the proximal section is radially offset from the at least one opening of the inner ring of the distal section.

* * * * *